(12) United States Patent
Canseco

(10) Patent No.: US 10,918,927 B2
(45) Date of Patent: Feb. 16, 2021

(54) SWING TRAINING DEVICE

(71) Applicant: Sport 40 40 LLC, Fort Worth, TX (US)

(72) Inventor: Jose Canseco, Las Vegas, NV (US)

(73) Assignee: Sports 40 40, LLC, Fort Worth, TX (US)

(*) Notice: Subject to any disclaimer, the term of this patent is extended or adjusted under 35 U.S.C. 154(b) by 0 days.

(21) Appl. No.: 15/767,075

(22) PCT Filed: Oct. 7, 2016

(86) PCT No.: PCT/US2016/056095
§ 371 (c)(1),
(2) Date: Apr. 9, 2018

(87) PCT Pub. No.: WO2017/062836
PCT Pub. Date: Apr. 13, 2017

(65) Prior Publication Data
US 2018/0304136 A1  Oct. 25, 2018

(51) Int. Cl.
A63B 69/00 (2006.01)
A61F 5/01 (2006.01)
A63B 69/36 (2006.01)

(52) U.S. Cl.
CPC .......... *A63B 69/0059* (2013.01); *A61F 5/013* (2013.01); *A63B 69/0002* (2013.01); *A63B 69/3623* (2013.01); *A61F 2005/0137* (2013.01); *A61F 2005/0158* (2013.01); *A61F 2005/0179* (2013.01); *A63B 2069/0008* (2013.01)

(58) Field of Classification Search
CPC ............ A63B 69/0002; A63B 21/0004; A63B 2069/0006; A63B 69/0059; A63B 69/3623; A63B 2069/0008; A61F 5/013; A61F 2005/0137; A61F 2005/0179
USPC ........ 473/450, 458, 464, 422, 438; 482/124, 482/141, 118, 130; 602/5, 16, 20, 21, 602/23–27
See application file for complete search history.

(56) References Cited

U.S. PATENT DOCUMENTS

| 4,559,932 A | * | 12/1985 | Salort | A61F 5/0118 602/20 |
| 4,614,181 A | * | 9/1986 | Karlsson | A61F 5/0125 602/16 |
| 4,715,363 A | | 12/1987 | Detty | |
| 4,875,677 A | | 10/1989 | Tetreault | |

(Continued)

FOREIGN PATENT DOCUMENTS

CN    1268880 A    10/2000

OTHER PUBLICATIONS

Office Action dated Jun. 19, 2019 from corresponding Canadian Application No. 3,001,454.

(Continued)

*Primary Examiner* — Mitra Aryanpour
(74) *Attorney, Agent, or Firm* — James E. Walton

(57) ABSTRACT

A swing training device has an upper cuff for removably receiving an upper arm of a user and a lower cuff for removably receiving a lower arm of the user. A hinge connects the cuffs, which are movable about the hinge and relative to each other between an extended position and a retracted position. An elastic member biases the cuffs toward the extended position. The device may be utilized for medical uses, such as for rehabilitation or strengthening exercises.

13 Claims, 4 Drawing Sheets

(56) References Cited

U.S. PATENT DOCUMENTS

| | | | |
|---|---|---|---|
| 5,133,341 A | 7/1992 | Singer et al. | |
| 5,135,469 A * | 8/1992 | Castillo | A61F 5/0123 602/16 |
| 5,337,737 A * | 8/1994 | Rubin | A63B 23/1281 482/111 |
| 5,403,002 A * | 4/1995 | Brunty | A61F 5/0123 473/438 |
| 5,788,618 A | 8/1998 | Joutras | |
| 6,117,097 A | 9/2000 | Ruiz | |
| 6,514,163 B2 | 2/2003 | Burns | |
| 6,537,237 B1 | 3/2003 | Hopkins et al. | |
| 6,932,724 B2 | 8/2005 | Socci | |
| 6,984,184 B2 | 1/2006 | Gray | |
| 7,048,704 B2 * | 5/2006 | Sieller | A61F 5/0125 602/16 |
| 7,122,016 B1 * | 10/2006 | DeToro | A61F 5/0125 602/26 |
| 7,207,960 B2 * | 4/2007 | Kenney | A61F 5/0125 128/878 |
| 7,309,322 B2 * | 12/2007 | Albrecht | A61F 5/0125 128/882 |
| 7,892,195 B2 * | 2/2011 | Grim | A61F 5/0585 128/846 |
| 8,216,168 B2 | 7/2012 | Farrell et al. | |
| 8,277,401 B2 * | 10/2012 | Hammerslag | A43C 11/14 2/22 |
| 8,292,760 B2 | 10/2012 | Johnson | |
| 8,517,965 B2 * | 8/2013 | Doty | A61F 5/0123 128/846 |
| 8,821,426 B2 * | 9/2014 | Einarsson | A61F 5/0106 602/23 |
| 8,926,455 B2 | 1/2015 | Drozjock et al. | |
| 9,668,903 B2 * | 6/2017 | Hsu | A61F 5/0123 16/345 |
| 2003/0065281 A1 | 4/2003 | Hopkins et al. | |
| 2004/0260219 A1 | 12/2004 | Jestrabek-Hart | |
| 2008/0108917 A1 * | 5/2008 | Joutras | A61H 1/024 601/34 |
| 2012/0264576 A1 * | 10/2012 | Goeckel | A63B 21/0004 482/124 |
| 2012/0271211 A1 * | 10/2012 | Bledsoe | A61F 5/0123 602/16 |
| 2014/0221889 A1 * | 8/2014 | Burns | A61F 5/0102 602/5 |
| 2014/0257156 A1 * | 9/2014 | Capra | A61F 5/0102 602/5 |
| 2016/0008157 A1 * | 1/2016 | Brookover | A61F 5/0123 602/16 |
| 2018/0028341 A1 * | 2/2018 | Martino | A61F 5/013 602/20 |
| 2018/0304136 A1 * | 10/2018 | Canseco | A61F 5/013 16/345 |

OTHER PUBLICATIONS

Office Action dated Jun. 29, 2020 from corresponding Chinese Application No. 201680061869.4.
Office Action dated Jan. 30, 2020 from corresponding Canadian Application No. 3,001,454.
Examination Report from corresponding Japanese Patent Appl. No. 2018-538065.
Office Action dated Aug. 26, 2020 from corresponding Canadian Application No. 3,001,454.

* cited by examiner

SWING TRAINING DEVICE

TECHNICAL FIELD

The present application relates to sports training aids, and in particular, to swing training devices for sports, such as baseball or golf, involving a swing.

DESCRIPTION OF THE PRIOR ART

Sports training devices provide assistance in performing or training for a movement utilized in a sport. Many training devices for baseball and/or softball batters and for golfers have been disclosed in the prior art. There are problems and limitations with each.

Although great strides have been made in the area of swing training devices, considerable shortcomings remain.

BRIEF DESCRIPTION OF THE DRAWINGS

The novel features believed characteristic of the system of the present application are set forth in the appended claims. However, the system itself, as well as a preferred mode of use, and further objectives and advantages thereof, will best be understood by reference to the following detailed description when read in conjunction with the accompanying drawings, wherein:

Figure 1:
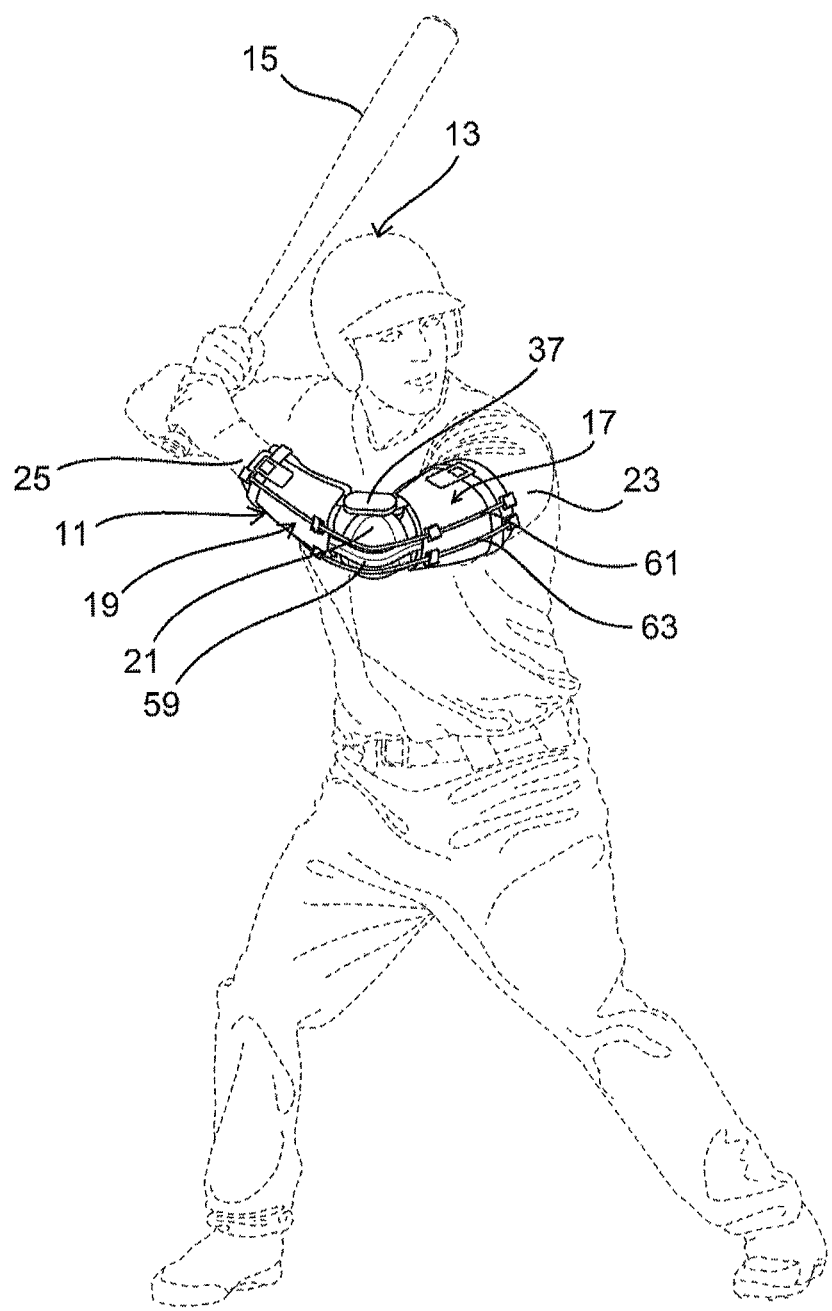
FIG. 1 is a perspective view of a swing training device according to the present application, the device being shown worn by a user.
Figure 2:
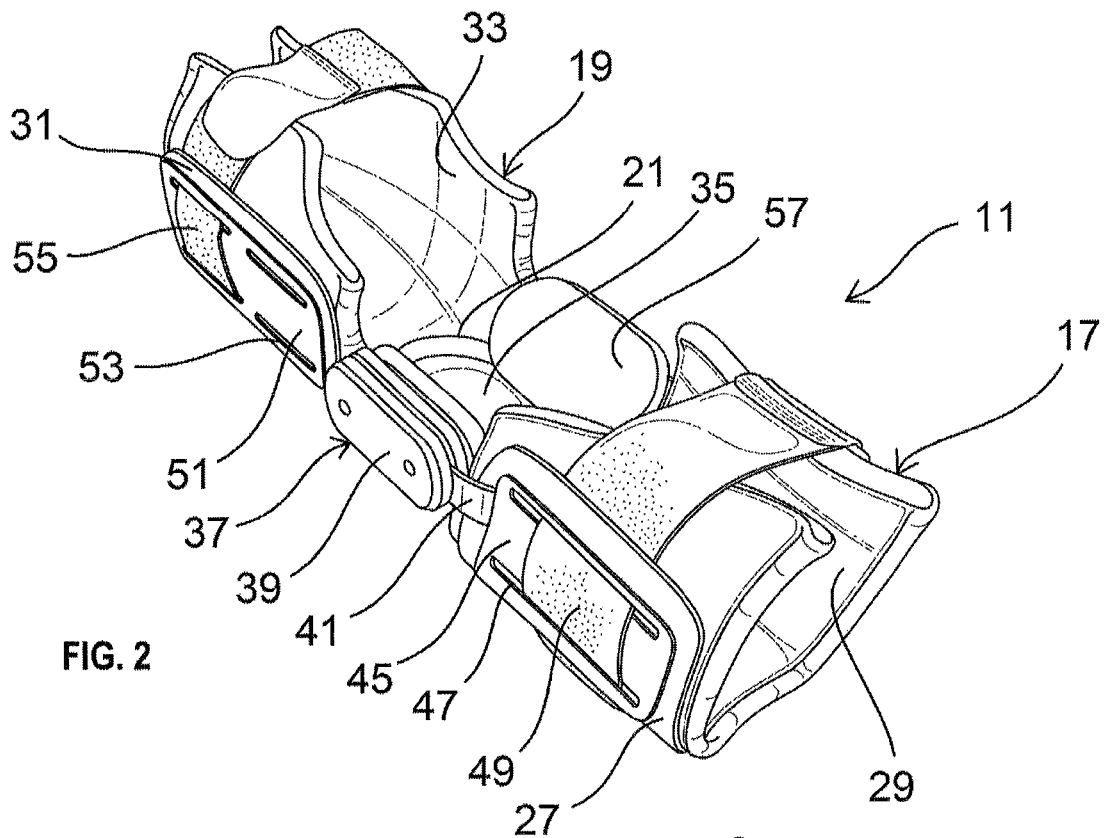
FIG. 2 is another perspective view of the training device of FIG. 1.
Figure 3:
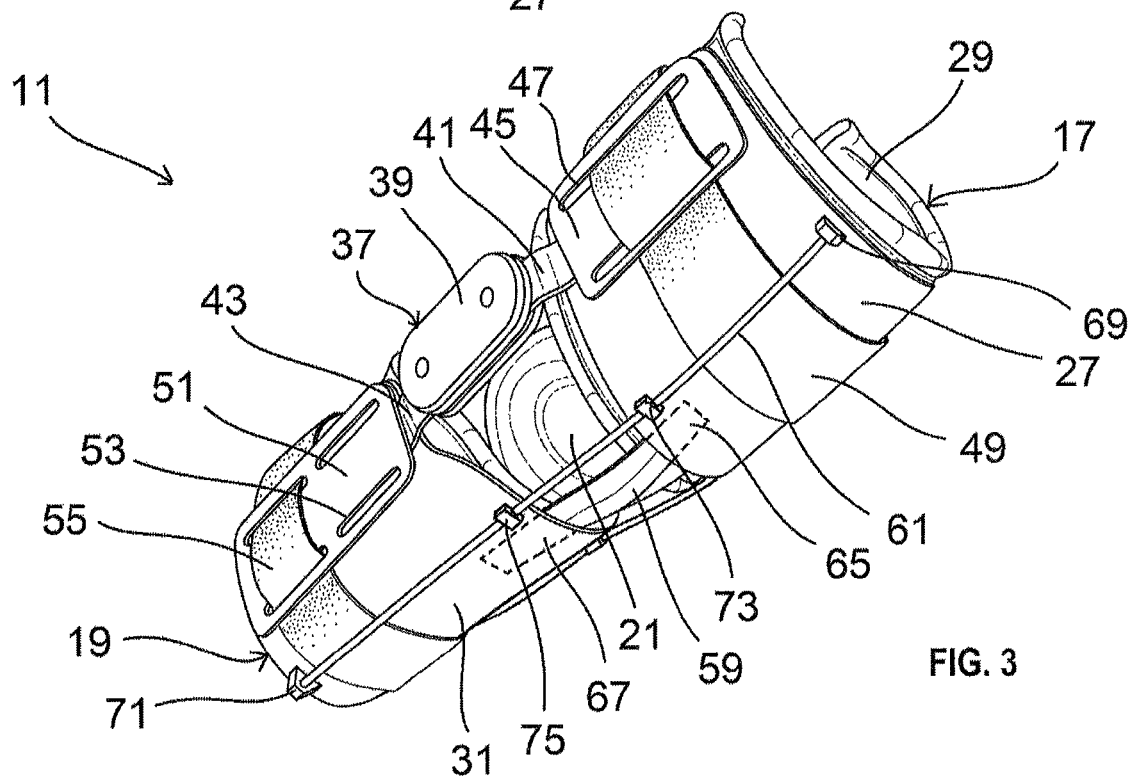
FIG. 3 is another perspective view of the training device of FIG. 1.
Figure 4:
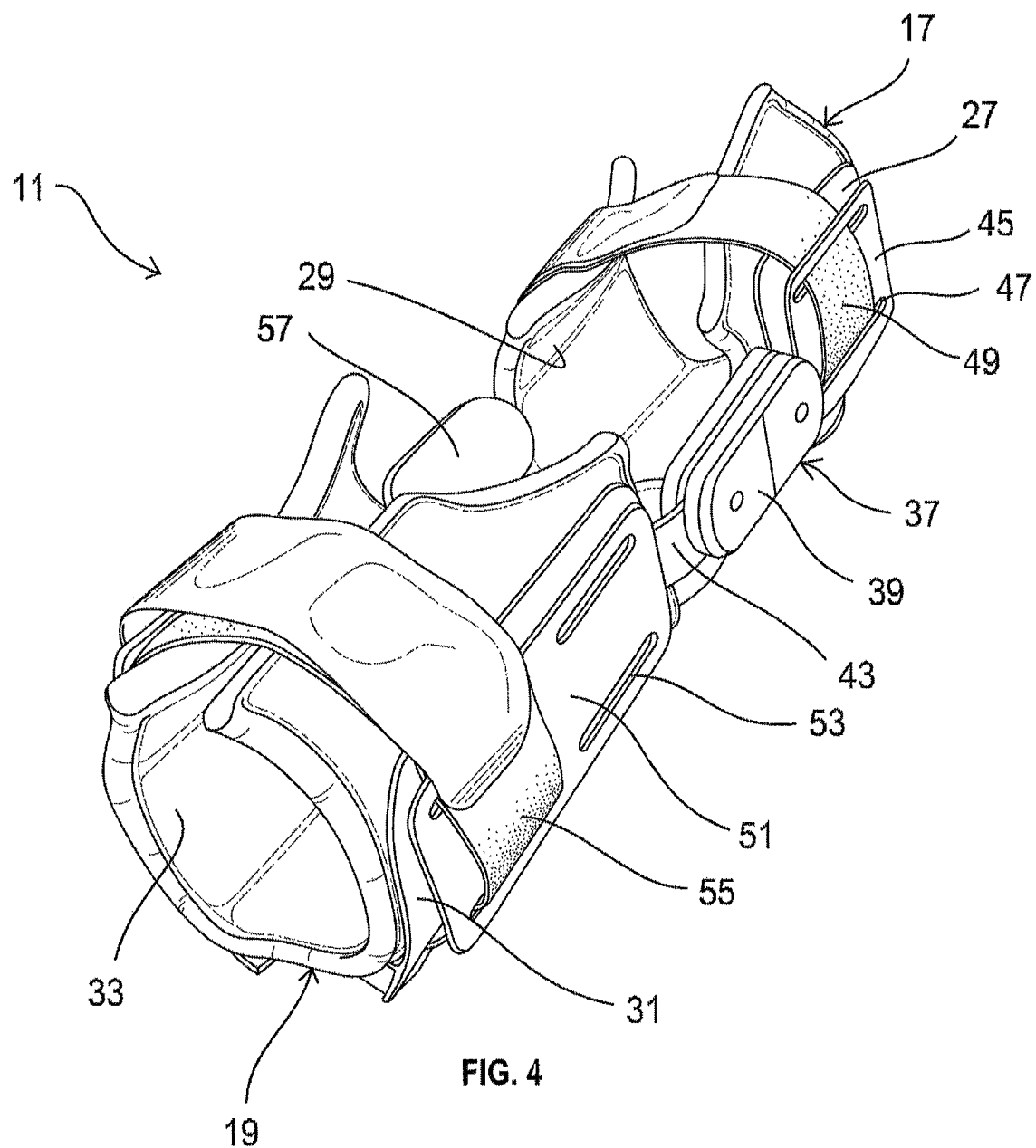
FIG. 4 is another perspective view of the training device of FIG. 1.
Figure 5:
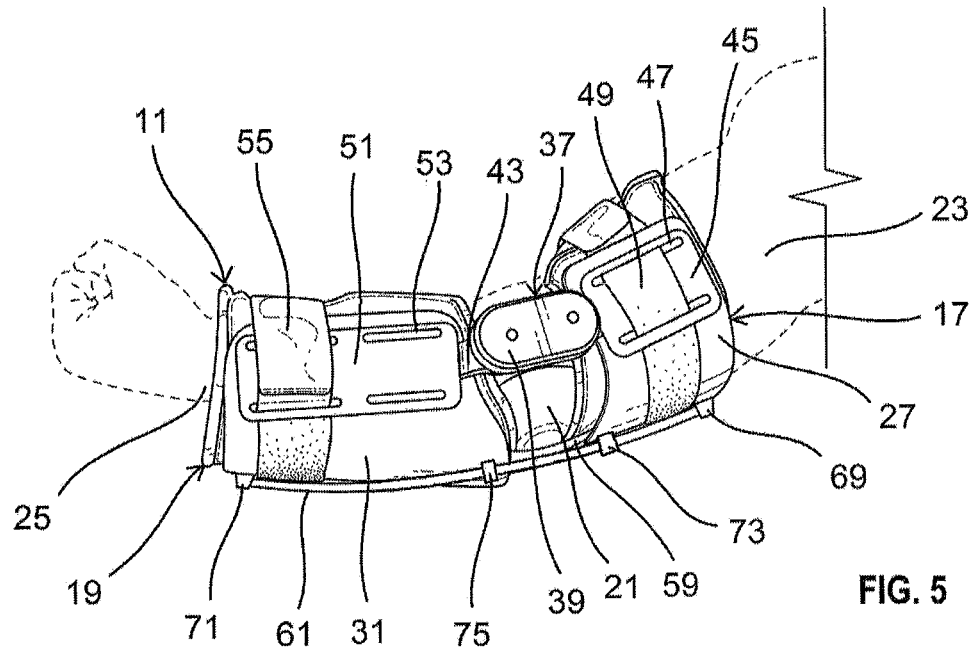
FIG. 5 is a perspective side view of the training device of FIG. 1, the training device being shown worn by a user and in an extended position.
Figure 6:
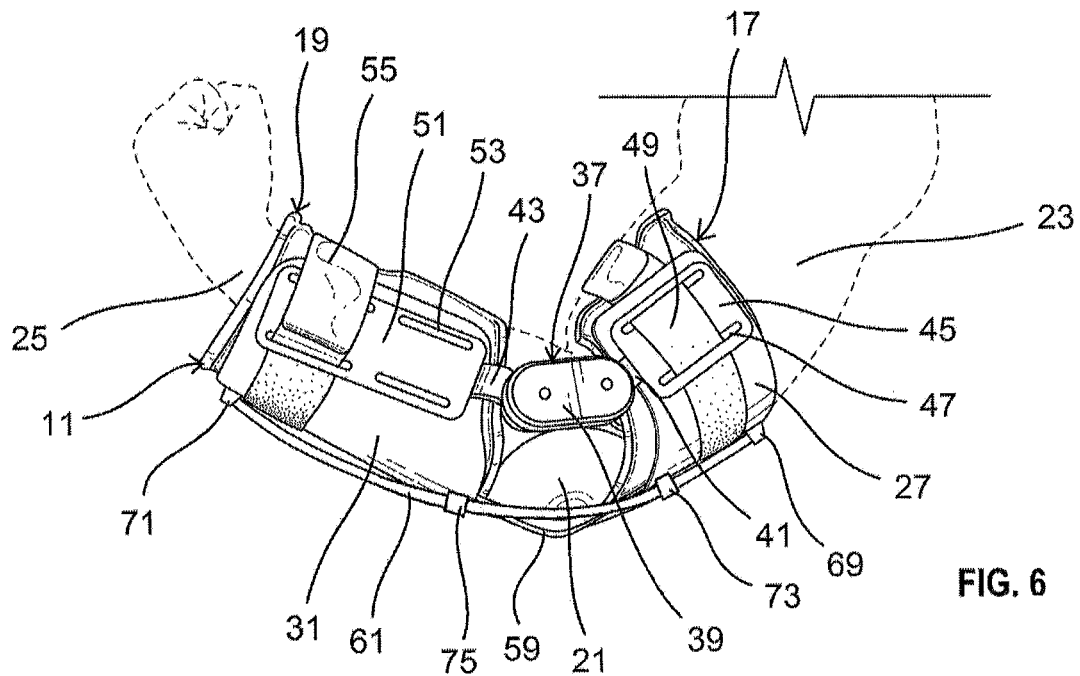
FIG. 6 is a perspective side view of the training device of FIG. 1, the training device being shown worn by a user and in a retracted position.

While the system of the present application is susceptible to various modifications and alternative forms, specific embodiments thereof have been shown by way of example in the drawings and are herein described in detail. It should be understood, however, that the description herein of specific embodiments is not intended to limit the method to the particular forms disclosed, but on the contrary, the intention is to cover all modifications, equivalents, and alternatives falling within the spirit and scope of the application as defined by the appended claims.

DESCRIPTION OF THE PREFERRED EMBODIMENT

Illustrative embodiments of the system of the present application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms, to describe a spatial relationship between various components or to describe the spatial orientation of aspects of such components should be understood to describe a relative relationship between the components or a spatial orientation of aspects of such components, respectively, as the device described herein may be oriented in any desired direction.

There is a need for an improved swing training device for athletes training for sports involving a swing, such as baseball, softball, and golf. The device is biased toward extension, thereby training users to fully extend the arm on which it is worn. In addition to swing training, the device may be utilized for medical uses, such as for rehabilitation or strengthening exercises.

FIGS. 1 through 6 illustrate a swing training device 11 according the present application. FIG. 1 shows a batter 13 holding bat 15 and wearing device 11, while positioned in a batting stance. Though shown in use by batter 13, device 11 may be appropriate for users participating in, or training for, other sports involving a swing, such as golf.

Device 11 comprises an upper cuff 17, a lower cuff 19, and an elbow pad 21. Cuffs 17, 19 are movable relative to each other between an extended position and a retracted, or bent, position, shown in FIGS. 1 and 6.

Upper cuff 17 is worn on an upper arm 23 of batter 13, and lower cuff 19 is worn on a lower arm 25 of batter 13. Elbow pad 21 is located between upper cuff 17 and lower cuff 19, and pad 21 is located adjacent an elbow of batter 13 when device 11 is worn. Elbow pad 21 may include an optional outer shell member. An upper outer shell 27 and inner padding 29 are operably associated with upper cuff 17; lower outer shell 31 and inner padding 33 are operably associated with lower cuff 19; and an inner padding 35 is operably associated with elbow pad 21. Padding 29, 33, 35 provides comfort for batter 13 and provides cushioning to reduce forces transferred to upper arm 23 and lower arm 25. Shells 27, 31 and elbow pad 21 are preferably formed from a semi-rigid material, such as a polymer, that is sufficient to resist significant deformation of the components during normal use while allowing for some deformation for obtaining a proper fit of device 11. In addition, it will be appreciated that shells 27, 31 and padding 29, 33, 35 may be formed of multiple layers of material, either like material or different material, and may include support members, stiffeners, stitching, adhesive, and other components and materials. Furthermore, padding 29, 33, 35 may be formed of, or treated with, a material that absorbs moisture, resists moisture, or wicks moisture away from the user.

Hinged braces 37 are located on opposite sides of device 11 for pivotally connecting upper cuff 17 and lower cuff 19. Each brace 37 has a central double hinge 39 with an upper element 41 and a lower element 43, each element 41, 43 pivoting separately relative to hinge 39. Each upper element 41 is rigidly coupled to an upper cuff plate 45, which has slots 47 for receiving an adjustable strap 49. Likewise, each lower element 43 is rigidly coupled to a lower cuff plate 51, which has slots 53 for receiving an adjustable strap 55. Inner padding 57 is preferably located at least on the inside of hinges 39. It will be appreciated that in some embodiments, it may be desirable to have a single hinge brace 37 on one side or the other of device 11.

Straps 49, 55 are preferably made of hook and loop material; however, it will be appreciated that straps 49, 55 may be made from a wide variety of materials, including elastic, flexible, semi-flexible, or rigid materials. Although strap 49 is shown passing through slots 47, it will be appreciated that straps 49 may be attached at one or more locations to upper element 41, upper cuff plate 45, and/or upper shell 27. Likewise, although strap 55 is shown passing through slots 53, it will be appreciated that straps 55 may be attached at one or more locations to lower element 43, lower cuff plate 51, and/or lower shell 31. Straps 49, 55 allow upper cuff 17 to be snugly wrapped around the user's upper arm, and lower cuff 19 to be snugly wrapped around the user's lower arm.

To control relative movement of cuffs 17, 19, hinges 39 may include a locking mechanism or other means for holding device 11 in the retracted position until a certain time and/or position in the swing of the user. In addition, hinges 39 may include a clutching mechanism, or restraint device, that slows extension of device 11, thereby allowing for use of device 11 during reduced-speed practice swings. For example, one or both hinges 39 may include dials, switches, buttons, and/or other adjustment mechanisms that allow the user to selectively adjust the operational parameters of hinges 39.

In order to provide the force for biasing device 11 toward the extended position, one or more biasing members, such as elastic bands, springs, and/or resilient members, extend between upper cuff 17 and lower cuff 19. In the embodiment shown, an elastic band 59 is located partially inside of device 11, and bands 61, 63 are located on the outside of device 11. Elastic bands 59, 61, 63 may be formed from any appropriate type of elastic material, such as elastomeric polymers or rubber, and may be of any construction, such as tubular or woven bands. Alternatively, bands 59, 61, 63 may be elastic springs formed from metal or another material, and elastic springs may include, for example, coil springs, elastic hinges, or leaf springs. It should be understood that in alternative embodiments, various types, shapes, and numbers of bands may be utilized at selected locations on device 11, to provide selected operational variations for device 11, thereby allowing the user to custom tailor his or her training, exercise, and/or rehabilitation.

In the embodiment shown, elastic band 59 is a flat band that is removably attached to the inner surface of upper shell 27 at location 65 and to the inner surface of lower shell 31 at location 67. Alternatively, band 59 may extend between the outer ends of cuffs 17, 19, in which case band 59 may be removably attached to cuffs 17, 19 with hooks or another system of attaching or fastening. Whether band 59 terminates within device 11 or extends to the ends of device 11, portions of band 59 located within cuffs 17, 19 are preferably located between padding 29, 33 and the associated shell 27, 31, thereby preventing band 59 from contacting upper arm 23 or lower arm 25 and causing discomfort to user 13.

More than one band 59 may be used, and each band 59 may be formed from one or more elastic elements. Each band 59 or element of band 59 may run directly over elbow pad 21 or may be positioned, such that band 59 runs beside pad 21. Another embodiment has at least two elastomeric bands 59 crossing each other in an X-pattern generally centered on elbow pad 21.

In the embodiment shown, elastomeric bands 61, 63 are tubular elastomeric bands, each band 61, 63 being attached at the ends to the outer surface of upper shell 27 at coupler 69 and to the outer surface of lower shell 31 at coupler 71. Alternatively, bands 61, 63 may extend between the outer ends of cuffs 17, 19, in which case bands 61, 63 may be removably attached to cuffs 17, 19 with hooks or another system of attaching or fastening. A single band 61 may be used on the outside of device 11, or more than one of each band 61, 63 may be used on each side of device 11. Bands 61, 63 may each be formed from one or more elastomeric elements, and each band 61, 63 may run directly over elbow pad 21 or may be positioned so that bands 61, 63 run on either side of pad 21, as shown. An upper guide 73 and lower guide 75 position each band 61, 63 in a selected path, along device 11, and preferably allow bands 61, 63 to translate therethough with minimal resistance.

For providing a single resistance level, bands 59, 61, 63 may be permanently attached to shells 27, 31. However, the preferred embodiments include removable and replaceable bands 59, 61, 63. One advantage to having bands 61, 63 on the outside of device 11 is that a user, while wearing device 11, can easily change bands 61, 63 for altered functional characteristics or for aesthetics. For example, bands 61, 63 of differing resistance may be replaced as desired to increase or decrease the biasing force for extending lower cuff 19, and this may be used to alter the force for different users or for changing the biasing force during stages of training or development. In addition, another embodiment may include the ability to move the location of couplers 69, 71 along the length of device 11 for increasing or decreasing the preload on bands 61, 63, thereby altering the resistance level without changing bands 61, 63.

Device 11 may be sold with multiples of each band 59, 61, 63, each band 59, 61, 63 offering a different resistance force, and this would allow the user to mix bands 59, 61, 63 to tailor the resistance to the desired level. In addition, or alternatively, additional bands 59, 61, 63 may be sold separately. Also, bands 59, 61, 63 may be offered in different colors, shapes, and/or patterns, for indicating the resistance level of each band 59, 61, 63 or in desirable colors and/or coordinated color schemes, such as, for example, in the colors of popular sports teams.

In operation, device 11, if so equipped, may first be configured by a user, such as batter 13, by selecting bands 59, 61, 63 having the desired combined resistance level. In addition, the user 13 may adjust the operational parameters of hinges 39 as desired. Device 11 is donned by inserting upper arm 23 in upper cuff 17 and inserting lower arm 25 in lower cuff 19 and then tightening straps 49, 55. In the extended position, as shown in FIGS. 2 through 5, bands 59, 61, 63 are in a relaxed condition, but in which elastic bands 59, 61, 63 may be preloaded with a biasing force toward the extended position. When batter 13 bends lower arm 25 toward upper arm 23, such as when moving to the batting stance shown in FIG. 1, lower cuff 19 moves with lower arm 25 and toward upper cuff 17 to the retracted, or bent, position shown in FIGS. 1 and 6. This stretches elastic bands 59, 61, 63, causing an increased biasing force toward the extended position and tend to cause lower arm 25 to extend with lower cuff 19 as batter 13 moves through the swing motion. Device 11 helps user 13 develop a proper and consistent swing motion.

The present application discloses a device having significant advantages, including: (1) providing a device for applying biasing force to a user's arm during swing training; (2) providing a swing training device that has adjustable biasing force; and (3) providing a device having adjustable force for rehabilitation or strength training.

The particular embodiments disclosed above are illustrative only, as the application may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the application. Accordingly, the protection sought herein is as set forth in the claims below. It is apparent that a system with significant advantages has been described and illustrated. Although the system of the present application is shown in a limited number of forms, it is not limited to just these forms, but is amenable to various changes and modifications without departing from the spirit thereof.

The invention claimed is:

1. A swing training device, comprising;
   an upper cuff configured to removably receive an upper arm of a user;
   a lower cuff configured to removably receive a lower arm of the user;
   a double hinge connecting the upper and lower cuffs, the upper and lower cuffs being movable about the double hinge and relative to each other between an extended position and a retracted position;
   a biasing member for biasing the upper and lower cuffs toward the extended position;
   an upper element disposed between a first hinge of the double hinge and the upper cuff;
   a lower element disposed between a second hinge of the double hinge and the lower cuff;
   an upper cuff plate attached to the upper element and supporting one or more upper adjustment straps for snugly securing the upper cuff to the user's upper arm; and
   a lower cuff plate attached to the lower element and supporting one or more lower adjustment straps for snugly securing the lower cuff to the user's lower arm;
   wherein the upper and lower adjustment straps wrap around the exterior of the upper and lower cuffs, respectively, have ends that overlap or are connected together, and are at least one of:
   received into slots of the upper and lower cuff plates, respectively; and
   attached to the upper and lower cuff plates, respectively;
   wherein the upper element is separate from the upper cuff and the upper cuff plate; and
   wherein the lower element is separate from the lower cuff and the low cuff plate.

2. The swing training device according to claim 1, wherein the biasing member comprises:
   an elastic band.

3. The swing training device according to claim 1, wherein the biasing member comprises:
   a plurality of similar elastic bands.

4. The swing training device according to claim 1, wherein the biasing member comprises:
   a plurality of dissimilar elastic bands.

5. The swing training device according to claim 1, wherein the biasing member is coupled to exterior portions of the upper cuff and the lower cuff.

6. The swing training device according to claim 1, wherein the biasing member is coupled to an interior surface of the upper cuff and to an interior surface of the lower cuff.

7. The swing training device according to claim 1, wherein the biasing member comprises:
   at least one elastomeric tube.

8. The swing training device according to claim 1, wherein the biasing member comprises:
   multiple elastomeric tubes.

9. The swing training device according to claim 8, wherein the elastomeric tubes are color coded to indicate differing elastomeric properties.

10. The swing training device according to claim 1, further comprising:
    at least one elbow pad disposed at least partially between the upper cuff and the lower cuff.

11. The swing training device according to claim 1, further comprising:
    an upper outer shell operably associated with the upper cuff; and
    a lower outer shell operably associated with the lower cuff.

12. The swing training device according to claim 1, wherein the slots of the upper and lower cuff plates comprise a first set of slots, further comprising:
    a second set of slots, comprising:
       one or more upper slots disposed in the upper cuff plate, the one or more upper adjustment straps extending through the one or more upper slots; and
       one or more lower slots disposed in the lower cuff plate, the one or more lower adjustment straps extending through the one or more lower slots.

13. The swing training device according to claim 1, wherein the upper and lower adjustment straps wrap around the exterior of the upper and lower cuffs, respectively, have ends that overlap and are connected together, are received into a first slot of the upper and lower cuff plates, respectively, and are received into a second slot of the upper and lower cuff plates, respectively.

* * * * *